United States Patent
Rollat et al.

(10) Patent No.: US 6,613,314 B1
(45) Date of Patent: Sep. 2, 2003

(54) RESHAPABLE HAIR STYLING COMPOSITION COMPRISING POLYURETHANE DISPERSIONS

(75) Inventors: Isabelle Rollat, Boulogne (FR); Henri Samain, Biévres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/627,785

(22) Filed: Jul. 27, 2000

(51) Int. Cl.$^7$ .............................. A61K 7/00; A61K 7/06
(52) U.S. Cl. ..................... 424/70.1; 424/70.11; 424/45; 424/47; 424/401; 424/78.03; 514/772.3
(58) Field of Search .............................. 424/70.1, 70.11, 424/45, 47, 484, 78.03, 401; 514/772.3

(56) References Cited

U.S. PATENT DOCUMENTS

| | | | |
|---|---|---|---|
| 3,479,310 A | 11/1969 | Dieterich et al. | 260/29.2 |
| 3,600,359 A | 8/1971 | Miranda | 260/77.5 |
| 3,700,643 A | 10/1972 | Smith et al. | 260/77.5 |
| 4,307,219 A | 12/1981 | Larson | 528/71 |
| 4,423,179 A | 12/1983 | Guagliardo | 524/539 |
| 4,507,430 A | 3/1985 | Shimada et al. | 524/839 |
| 4,542,012 A | 9/1985 | Dell | |
| 4,558,149 A | 12/1985 | Larson | |
| 4,667,661 A | 5/1987 | Scholz et al. | 128/90 |
| 4,699,133 A | 10/1987 | Schafer et al. | 128/156 |
| 4,738,992 A | 4/1988 | Larson et al. | 521/157 |
| 4,746,717 A | 5/1988 | Larson | 528/68 |
| 4,798,721 A | 1/1989 | Yahagi et al. | 424/70 |
| 4,978,527 A | 12/1990 | Brink et al. | |
| 4,985,239 A | 1/1991 | Yahagi et al. | 424/70 |
| 5,045,601 A | 9/1991 | Capelli et al. | |
| 5,120,531 A | 6/1992 | Wells et al. | |
| 5,173,291 A | 12/1992 | Brink et al. | |
| 5,180,061 A | 1/1993 | Khan et al. | |
| 5,230,701 A | 7/1993 | Meyer et al. | 602/76 |
| 5,302,385 A | 4/1994 | Khan et al. | |
| 5,334,650 A | 8/1994 | Serdiuk et al. | 524/591 |
| 5,334,690 A | 8/1994 | Schafheutle et al. | 528/71 |
| 5,334,691 A | 8/1994 | Gould et al. | 528/76 |
| RE34,730 E | 9/1994 | Salatin et al. | 427/404 |
| 5,370,910 A | 12/1994 | Hille et al. | 427/407.1 |
| 5,610,232 A | 3/1997 | Duan et al. | |
| 5,616,400 A | 4/1997 | Zhang | 428/195 |
| 5,626,840 A * | 5/1997 | Thomaides et al. | 424/70.11 |
| 5,643,581 A | 7/1997 | Mougin et al. | 424/401 |
| 5,650,159 A | 7/1997 | Lion et al. | 424/401 |
| 5,672,653 A | 9/1997 | Frisch et al. | 524/591 |
| 5,679,754 A | 10/1997 | Larson et al. | 528/28 |
| 5,692,937 A | 12/1997 | Zhang | 442/149 |
| 5,843,523 A | 12/1998 | Mazza et al. | 427/208.8 |
| 5,855,208 A | 1/1999 | Askill et al. | |
| 5,874,072 A | 2/1999 | Alwattari et al. | 424/70.7 |
| 5,879,668 A | 3/1999 | Hanna et al. | 424/70.7 |
| 5,911,973 A | 6/1999 | de la Poterie | 424/61 |
| 5,925,724 A | 7/1999 | Cenens et al. | 528/85 |
| 5,951,993 A | 9/1999 | Scholz et al. | 424/405 |
| 5,962,620 A | 10/1999 | Reich et al. | 528/76 |
| 5,968,494 A * | 10/1999 | Kukkala et al. | 424/70.1 |
| 5,968,495 A | 10/1999 | Bolich, Jr. et al. | |
| 5,972,354 A | 10/1999 | de la Poterie et al. | 424/401 |
| 5,981,650 A | 11/1999 | Zhao et al. | 524/591 |
| 5,989,570 A | 11/1999 | Lion et al. | 424/401 |
| 5,993,972 A | 11/1999 | Reich et al. | 428/423.1 |
| 5,997,886 A | 12/1999 | Peffly et al. | |
| 6,007,793 A | 12/1999 | Bhatt et al. | 424/47 |
| 6,165,239 A | 12/2000 | Hedrick et al. | |
| 6,319,959 B1 | 11/2001 | Mougin et al. | |

FOREIGN PATENT DOCUMENTS

| | | |
|---|---|---|
| EP | 0 039 162 A2 | 11/1981 |
| EP | 0 299 148 A2 | 1/1989 |
| EP | 0 636 361 | 2/1995 |
| EP | 0 637 600 | 2/1995 |

(List continued on next page.)

OTHER PUBLICATIONS

English language translation of JP 10–203937, Aug. 4, 1998, pp. 1–11.

Derwent Abstract of EP 0 637 600, Aug. 8, 1995, pp. 1–23.

Derwent Abstract of EP 0 751 162, Jan. 2, 1997, pp. 1–30.

Derwent Abstract of EP 0 938 889 Feb. 9, 1999, pp. 1–16.

Derwent Abstract of EP 0 957 119, Nov. 17, 1999, pp. 1–25.

Derwent Abstract of JP 10–203937 637 600, Aug. 4, 1998, pp. 1–10.

*Primary Examiner*—Thurman K. Page
*Assistant Examiner*—Rachel M. Bennett
(74) *Attorney, Agent, or Firm*—Finnegan, Henderson, Farabow, Garrett & Dunner, L.L.P.

(57) ABSTRACT

A reshapable hair styling composition comprising, in a cosmetic vehicle appropriate for hair, at least one dispersion comprising at least one polyurethane in a water and/or solvent medium, said at least one polyurethane being obtained by reacting:

(a) an isocyanate terminated polyurethane prepolymer being obtained by reacting: (i) at least one polyactive hydrogen compound insoluble in the medium of the dispersion, wherein said polyactive hydrogen compound is chosen from alkyl, aryl, and aralkyl structures optionally substituted in and/or on the structure by N, O, and/or S groups; (ii) at least one polyisocyanate, and (iii) at least one polyactive hydrogen compound soluble in the medium of the dispersion, (b) at least one polyfunctional chain extender; and (c) at least one chain terminator.

27 Claims, No Drawings

FOREIGN PATENT DOCUMENTS

| | | |
|---|---|---|
| EP | 0 656 021 | 6/1995 |
| EP | 0 696 607 | 2/1996 |
| EP | 0 751 162 | 1/1997 |
| EP | 0 779 310 | 6/1997 |
| EP | 0 807 647 A1 | 11/1997 |
| EP | 0 838 211 | 4/1998 |
| EP | 0 838 212 | 4/1998 |
| EP | 0 937 451 | 8/1999 |
| EP | 0 938 889 | 9/1999 |
| EP | 0 957 119 | 11/1999 |
| EP | 1 068 859 | 1/2001 |
| FR | 2 782 637 | 3/2000 |
| JP | 10-203937 | 8/1998 |
| WO | WO 94/03510 | 2/1994 |
| WO | WO 94/13724 | 6/1994 |
| WO | WO 96/14049 | 5/1996 |
| WO | WO 97/17052 | 5/1997 |
| WO | WO 97/17386 | 5/1997 |
| WO | WO 98/38969 | 9/1998 |
| WO | WO 99/39688 | 8/1999 |
| WO | WO 99/43289 | 9/1999 |
| WO | WO 99/47127 | 9/1999 |
| WO | WO 99/48941 | 9/1999 |
| WO | WO 99/58100 | 11/1999 |
| WO | WO 99/63955 | 12/1999 |

* cited by examiner

RESHAPABLE HAIR STYLING COMPOSITION COMPRISING POLYURETHANE DISPERSIONS

The present invention relates to a reshapable hair styling composition.

Fixing the hairstyle is an important element in hair styling, and involves maintaining a shaping that has already been carried out, or in simultaneously shaping and fixing the hair.

In accordance with the invention, the term "hair styling composition" relates to any kind of hair composition that can be used to effect hair styling, for example fixing compositions, shampoos, conditioners, permanent waving compositions, hair care products, and hair treatment products.

The most prevalent hair styling compositions on the cosmetic market for shaping and/or maintaining the hairstyle are spray compositions comprising a solution, usually alcohol- or water-based, and one or more materials, generally polymer resins. One of the functions of polymer resins is to form links between the hairs, these materials also being called fixatives, in a mixture with various cosmetic adjuvants. This solution is generally packaged either in an appropriate aerosol container, which is pressurized with the aid of a propellant, or in a pump flask.

Other known hair styling compositions include styling gels and mousses, which are generally applied to the wetted hair before brushing or setting it. In contrast to the conventional aerosol lacquers, these compositions have the disadvantage that they do not allow the hair to be fixed in a shape created before their application. In fact, these compositions are essentially aqueous and their application wets the hair and is therefore unable to maintain the initial shape of the hairstyle. In order to shape and fix the hairstyle, therefore, it is necessary to carry out subsequent brushing and/or drying.

Such hair styling compositions all have the same disadvantage that they do not allow the hairstyle to be later modified to a desired shape, which is other than that formed initially, without starting the styling and fixing operations again. Moreover, under various kinds of stress, the hairstyle has a tendency to take on an undesirable permanent set, which cannot easily be modified. Also in the styling process, one desires hair conditioning benefits, such as ease of combing and soft hair feel appearance.

A subject of the invention is a reshapable hair styling composition comprising, in a cosmetic vehicle appropriate for hair, at least one polyurethane.

Another subject of the invention is a reshapable hair styling composition comprising, in a cosmetic vehicle appropriate for hair, at least one dispersion comprising at least one polyurethane.

Another subject of the invention is a reshapable hair styling composition comprising, in a cosmetic vehicle appropriate for hair, at least one dispersion comprising at least one polyurethane and a water and/or solvent medium of dispersion.

Another subject of the invention is a reshapable hair styling composition comprising, in a cosmetic vehicle appropriate for hair, at least one dispersion comprising at least one polyurethane in a water and/or solvent medium of dispersion, said at least one polyurethane being obtained by reacting:

(a) an isocyanate terminated polyurethane prepolymer being obtained by reacting: (i) at least one polyactive hydrogen compound insoluble in said medium of dispersion, wherein said polyactive hydrogen compound is selected from alkyl, aryl, and aralkyl structures optionally substituted in and/or on the structure by N, O, and/or S groups; (ii) at least one polyisocyanate, and (iii) at least one polyactive hydrogen compound soluble in the medium of the dispersion, (b) at least one polyfunctional chain extender; and (c) at least one chain terminator.

The medium of dispersion can be, for example, an alcohol mixture or a water/alcohol mixture.

The term "reshapable" hair styling composition means a hair styling composition providing hair styling that can be restored or modified without new material or heat being applied. For example, in order to restore or modify the hairstyle in case of "drooping" or loss of setting (dishevelment), no new materials, such as water or any form of fixing agent, or heat are required. Thus, to provide a "reshapable" effect means to provide a hair styling that can be restored or modified without new material or heat being applied. The efficacy of the composition can be long lasting, such as 10–24 hours, giving rise to a durable styling effect. Other terms, which may be synonymous with reshapable, include repositionable, remoldable, restyleable, and remodellable.

It is a further subject of the invention to provide a method for treating hair, characterized in that the composition according to the invention is applied to the hair before, during, or after shaping the hairstyle.

As used herein, a "dispersion" means generally a two-phase system where one phase comprises discrete particles distributed throughout a bulk substance, the particles being the disperse or internal phase, and the bulk substance the continuous or external phase. In an embodiment of this invention, at least a portion of the polyurethane exists as the discrete particle in the continuous phase. The term "dispersion" does not necessarily mean that the entire polyurethane polymer needs to be insoluble; at least some of the polymer can be soluble in the medium. Dispersions may result from the use of certain components that are insoluble in the solvent system. It is desirable that the dispersion remains stable under ambient conditions. In one embodiment, the dispersions are stable at room temperature for more than 30 days, also for more than 90 days, further also for more than 180 days, and more further also for more than 360 days.

The polyurethane dispersion may be made by forming the isocyanate terminated polyurethane prepolymer, chain extending the prepolymer, and chain terminating the prepolymer to yield a polyurethane polymer that may be stable and dispersed in the water and/or solvent system. Although it is possible to carry out the foregoing steps sequentially, this is not necessary. The order of the steps may be changed and certain steps can be combined, such as chain extension and chain termination or prepolymer formation and chain termination. For example, an excess of chain extender can also serve as the chain terminator. The steps and the components are discussed in detail below.

As used herein the term "isocyanate terminated polyurethane prepolymer", or alternately referred to as "isocyanate functional polyurethane prepolymer" means a reaction product of a mixture comprising at least one polyisocyanate, at least one medium insoluble polyactive hydrogen compound, and at least one medium soluble polyactive hydrogen compound. In general, the reaction occurs with a molar excess of isocyanate groups to produce an oligomer, which may have urethane, urea, and/or thiourethane functional groups. The prepolymer can be prepared at an equivalent ratio of isocyanate groups to active hydrogen reactive groups of greater than 1.6:1, also greater than 1.8:1, and further also about 2.0:1 or greater.

As used herein, the term "polyactive hydrogen compound" means a compound having an average functionality greater than 1, such as greater than 1.8, and further such as about 2.0 or greater but less than about 6, such as less than about 4, and further such as about 3 or less. The term is understood to include compounds that have (i) alcohol groups on primary, secondary, and tertiary carbon atoms, (ii) primary and secondary amines, (iii) mercaptans, and (iv) mixtures of these functional groups.

Accordingly, the inventive polyurethane dispersions can contain urea linkages, e.g., from the reaction of isocyanate functional polyurethanes with amines, these polymers more appropriately being labeled as "polyurethane-ureas".

The polyactive hydrogen compounds useful for preparing the prepolymer have a molecular weight of 62 to 10,000, also 200 to 5,000, and further also 400 to 3,000.

The "A component," also referred to as the (a)(i) component, i.e., the medium insoluble polyactive hydrogen compound, may generally be present at concentrations of at least 5% by weight, also at least 10% by weight, and further also at least 20% by weight of the total of components (a)(i), (a)(ii), and (a)(iii). The phrase "medium insoluble" means generally that at least 1 gram of the compound is not soluble in about 4 grams of the medium of the dispersion at about 25° C. Certain polyactive hydrogen compounds may require heating to melt to determine whether they are soluble or insoluble using this characterization method.

Several different types of polyols are suitable for use as the "A component," generally including polyols chosen from those having alkyl, aryl, and aralkyl structures optionally substituted in and/or on the structure by N, O, and/or S groups. The compounds generally useful as the "A component" may have a number average molecular weight at least above about 300, such as above about 400, and further such as above about 500. But such compounds may have a number average molecular weight at least below about 10,000, such as below about 5,000, and further such as below about 3,000.

Monomeric polyols, such as the $C_{36}$ dimer fatty alcohol available as PRIPOL 2033 from Uniqema North America, Chicago, Ill., can be used. Oligomeric polyols having, on average, from about 1.6 to about 4 hydroxyl or amino groups can also be used. One embodiment of an oligomeric polyol useful as the "A component" is aliphatic polyester polyol based on diacids and/or diols that have greater than 10 carbon atoms, such as greater than 20 carbon atoms. Commercial examples of polyester polyols are PRIPLAST 3191, 3192, 3196, 3197,1906, and 1907 from Uniqema North America, Chicago, Ill., believed to be based on a 36 carbon atom diacid and/or diol. Specific constituents used in preparation of these diols are believed to be for PRIPLAST 3192—dimer acid, adipic acid, and 1,6-hexane diol; for PRIPLAST 3193—dimer acid and ethylene glycol; for PRIPLAST 3194—dimer acid, adipic acid, and ethylene glycol; for PRIPLAST 3196—dimer acid and 1,6-hexane diol; for PRIPLAST 3197—dimer acid and dimer diol; for PRIPLAST 1906—isophthalic acid and dimer diol; and for PRIPLAST 1907—terephthalic acid and dimer diol. Another embodiment of an oligomeric polyol is hydroxy terminated polyalkadienes, including polybutadienes and polyisoprenes, such as POLY bd resin from Elf Atochem North America, Philadelphia, Pa.

An oligomeric polyol may be chosen from hydrogenated polyalkadiene polyols, including hydrogenated polyisoprene and hydrogenated polybutadiene, the latter having no less than 19 wt % 1,2-butadiene addition. Commercial examples of hydrogenated polybutadiene diols include KRATON L-2203 from Shell Chemical, Houston, Tex., and POLYTAIL resins from Mitsubishi Chemical, Tokyo, Japan.

In another embodiment, the "A component" is an oligomeric polyamine. Suitable oligomeric polyamines include amine terminated butadiene polymers and butadiene-acrylonitrile copolymers. A commercial example of such an amine is HYCAR ATBN from B. F. Goodrich, Cleveland, Ohio.

Silicone polyols and perfluoroalkyl functional polyols, when used, should not be present in greater than about 5 weight percentage of the overall composition as their low surface energy properties would be expected to detract from the desired adhesion characteristics based on the teachings of U.S. Pat. No. 5,679,754 (Larson et al.), whose disclosure is incorporated herein by reference.

Representative polyisocyanates that can be used to form the isocyanate functional polyurethane include aliphatic, cycloaliphatic, and aromatic polyisocyanates. Suitable aliphatic polyisocyanates include aliphatic isocyanates and diisocyanates. Diisocyanates may, for example, be chosen from dicyclohexylmethane 4,4'-diisocyanate (commonly referred to as $H_{12}MDI$) and 3,5,5-trimethyl-1-isocyanato-3-isocyanatomethylcyclohexane (commonly referred to as isophorone diisocyanate or IPDI), both available from Bayer Corp., Pittsburgh, Pa., under the trade designations DESMODUR W and DESMODUR I, respectively. In addition, diisocyanates may be chosen from (i) tetramethylene diisocyanate, (ii) 1,3-bis(isocyanatomethyl) cyclohexane, (iii) 1,3-bis(1-isocyanato-1-methylethyl)benzene, (iv) diphenylmethane 4,4'-diisocyanate (commonly referred to as MDI), (v) 4,4',4''-triisocyanatotriphenyl methane, (vi) polymethylene polyphenylene polyisocyanate (commonly referred to as polymeric MDI), (vii) toluene diisocyanate (commonly referred to as TDI), (viii) hexamethylene diisocyanate (commonly referred to as HDI), (ix) dodecamethylene diisocyanate, and (x) m- and p-xylene diisocyanate.

Other useful polyisocyanates include those described in U.S. Pat. No. 3,700,643 (Smith et al.) and U.S. Pat. No. 3,600,359 (Miranda), whose disclosures are incorporated herein by reference. Mixtures of polyisocyanates can also be used, such as ISONATE 2143L, available from Dow Chemical Co., Midland, Mich.

The polyurethane prepolymer is made dispersible in the medium by using a "B component", also referred to as the (a)(iii) component, i.e., the at least one medium soluble polyactive hydrogen compound. That is, the B component may act to stabilize the polyurethane dispersion in the medium. The phrase "medium soluble" means generally that at least 1 gram of the compound is soluble in about 4 grams of the medium at about 25° C. Certain compounds may require heating to melt to determine whether they are soluble or insoluble using this characterization method. The medium used in this characterization method should be the same medium used to prepare the dispersing medium. For example, alcohol-water solubility may be imparted to this compound by the presence of an ionic group, a moiety capable of forming an ionic group, or a polyester, polyether, or polycarbonate group having a ratio of 5:1 or less, such as 4:1 or less, carbon atoms for each oxygen atom, and mixtures thereof.

When present, the ionic group of the B component may be chosen from anionic, cationic, and zwitterionic groups. The cationic groups may originate from the isocyanate or polyol component but most conveniently are added in as a polyol component. The cationic group may be incorporated directly into the prepolymer. For example, a quaternary diol such as VARIQUAT 1215 may be reacted into the prepolymer directly. Alternatively, a precursor group can be reacted into the prepolymer and then be rendered cationic in a subsequent reaction. For example, active hydrogen functional tertiary amines, such as methyldiethanolamine and its polyethoxylated adducts may be incorporated into the prepolymer backbone and subsequently protonated with a mineral or organic acid to form an ionic salt or alkylated to form a quaternary ammonium group. Reaction of the incorporated tertiary amine with hydrogen peroxide, propane sultone, or lactone gives zwitterionic moieties. Stabilizing cationic components may be very water-soluble, generally having a solubility in water of at least 1% by weight, such as in excess of 10% by weight. Stabilizing cationic compounds may have the following structure:

$$R\text{—}N^+(R_2)[(OCH_2CH_2)_nOH]_2X^-$$

where R is chosen from $C_1$–$C_{18}$ alkyl, $C_6$–$C_{18}$ aryl, and $C_6$–$C_{18}$ aralkyl structures optionlly substituted in and/or on the structure by N, O, and/or S groups; $R_2$ is chosen from a hydrogen atom and $C_1$–$C_{18}$ alkyl groups; n is an integer from about 1 to about 200, such as about 1 to about 50, and further such as about 1 to about 20; and $X^-$ is chosen from halides, sulfates, methosulfates, ethosulfates, acetates, carbonates, and phosphates.

Cationic stabilizing compounds may be chosen from protonated and alkylated methyl diethanol amines as well as PEG 2 cocomonium chloride and PEG-15 cocomonium chloride available from Witco/Sherex as VARIQUAT 638 and VARIQUAT K1215 respectively.

It is possible to incorporate cationic compounds that have a single reactive hydrogen group. However, they are not considered optimal.

The anionic stabilizer used in the present invention can be present on either the isocyanate component or the polyactive hydrogen component. Typically, and most conveniently, the anionic stabilizer is present as a polyol component. The anionic group can be chosen from sulfonates, phosphonates, phosphates, and carboxylates; also from sulfonates and carboxylates; and further also from sulfonates. The sulfonates may be chosen from the sulfonated polyols described in U.S. Pat. No. 4,738,992 (Larson et al.), whose disclosure is incorporated herein by reference. The sulfonates include polyesterdiols having the following structure:

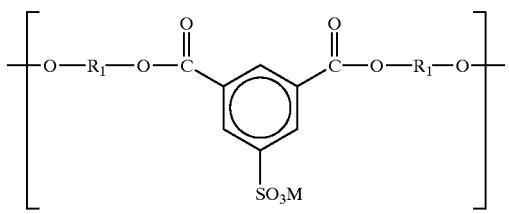

wherein M is a cation chosen from H, alkali metals, alkaline earth metals, and primary, secondary and tertiary ammonium cations, such as ammonium, methylammonium, butylammonium, diethylammonium, triethylammonium, tetraethylammonium, and benzyltrimethylammonium cations; and each $R_1$ is the same or different and chosen from divalent aliphatic groups having an average molecular weight of about 200 to about 600 comprising ether and/or ester functional groups chosen from:

—$CH_2$—$CH_2$—$(OCH_2$—$CH_2$—$)_n$—,

—$C(CH_3)H$—$CH_2$—$(OC(CH_3)H$—$CH_2$—$)_n$—,

—$(CH_2)_4$—$(O(CH_2)_4)_n$—, and

—$(CH_2)_m$—CO—[—O—$(CH_2)_m$—CO—$]_n$— groups;

where m is an integer from about 2 to about 5; and n is an integer from about 2 to about 15.

Suitable carboxylate and carboxylic acid functional polyols include dimethylolpropionic acid and its polyethoxylated derivatives as well as acid grafted polyethers such as the UCARMOD polyols available from Union Carbide Specialty Chemicals Div., Danbury, Conn. These can be neutralized with an organic or inorganic base either before or after preparation of the prepolymer.

In one embodiment, to obtain alcohol-water or water dispersibility, the ionic equivalent weight of the prepolymer (gram prepolymer per equivalent of ionic functionality) should be in the range of about 1000 g/equiv to about 15000 g/equiv, also about 1500 g/equiv to about 12500 g/equiv, further also about 2000 g/equiv to about 10000 g/equiv, and more further also about 2500 g/equiv to about 7500 g/equiv.

Examples of oligomeric polyactive hydrogen compounds that have sufficient polar non-ionic groups such as ether or ester functionality that provides a ratio of 5 or less carbon atoms for each oxygen atom to give alcohol-water solubility include (i) polyoxyalkylene diols, triols, and tetrols, (ii) polyoxyalkylene diamines and triamines, (iii) polyester diols, triols, and tetrols of organic polycarboxylic acids and polyhydric alcohols, and (iv) polylactone diols, triols, and tetrols having a molecular weight of about 106 to about 2000. Examples of oligomeric polyols and polyamines include (i) polyethylene oxide homopolymers (e.g., CARBOWAX series from Union Carbide, Danbury, Conn.), block copolymers of ethylene oxide and propylene oxide (e.g., PLURONIC surfactants from BASF Corporation, Mount Olive, N.J.), random copolymers of ethylene oxide and propylene oxide (e.g., UCON FLUIDS from Union Carbide, Danbury, Conn.), silicone copolyols, as well as surfactants based on polyethylene oxide as described in U.S. Pat. No. 4,667,661 (Scholz et al.), whose disclosure is incorporated herein by reference, (ii) polyoxypropylene diols and triols such as the ACCLAIM series of polyols from Arco Chemical, Newtown Square, Pa., (iii) polyether diamines, and triamines such as the JEFFAMINE series available from Huntsman Corporation, Salt Lake City, Utah, (iv) polyether polyols such as the TERATHANE series (which is a polyoxytetramethylene diol) available from E.I. du Pont Co., Wilmington, Del., and the POLYMEG series available from Quaker Oats Co., Chicago, Ill., (v) polyester polyols such as MULTRON, which is a poly (ethyleneadipate) polyol, available from Bayer Corporation, Pittsburgh, Pa., (vi) polycarbonate diols such as those available from Stahl USA Co., Peabody, Mass., and (vii) polycaprolactone polyols such as the TONE series available from Union Carbide, Danbury, Conn. Polythioether polyols are also useful.

In addition, when alcohol insoluble polyols are used, low molecular weight medium soluble "monomeric" polyols may be used. Examples of the monomeric polyols include ethylene glycol, propylene glycol, butylene glycol, hexamethylene glycol, diethylene glycol, 1,1,1-trimethylolpropane, pentaerythritol, aminoethanol, and the like. When used, the amount of the monomeric polyols should be kept low to minimize the viscosity of the prepolymer.

The reaction of the components discussed above (i.e., the A component, the polyisocyanate, and the B component) to form the prepolymer will depend on the specific components chosen. Aromatic isocyanates are generally much more reactive than aliphatic isocyanates and may be reacted with polyols without the need for heat because the reaction will be exothermic. The reaction may be run as 100% solids (i.e., little to no solvent) or may be carried out in an optionally polar organic solvent unreactive with the isocyanate. Such solvents include, for example, acetone, methyl ethyl ketone (MEK), methoxypropanol acetate (PM acetate), dimethyl acetamide, tetrahydrofuran, N-methyl-pyrrolidinone, and mixtures thereof. In one embodiment, the solvent used will not require removal in the final composition. It is also possible to incorporate solvents and/or plasticizers that are left in the prepolymer that become part of the finished dispersion.

When using aliphatic isocyanates with polyfunctional alcohols, high solids concentrations and elevated reaction temperatures from about 50° C. to about 80° C. are desirable so that high conversions of monomers to polymer can occur in a reasonable time, e.g., less than eight hours, also less than three hours. Embodiments incorporating isophorone diisocyanate or hexamethylene diisocyanate and aliphatic primary or secondary alcohols are typically heated to about 80° C. for about 2 hours in the presence of a small amount of catalyst.

Useful catalysts include metal salts such as dibutyltin dilaurate and dibutyltin diacetate, and amines, such as triethylamine, DBU (1,8-diazabicyclo[5.4.0] undec-7-ene), and DABCO (1,4-diazabicyclo[2.2.2]octane), in useful concentrations of from about 0.01 to about 1.0 mole percent (relative to the isocyanate reagent). In one embodiment, catalysts are non-irritating and non-sensitizing to skin. The catalysts may be chosen from those that can become bound to the polymer backbone and are thus non-leachable, such as FASTCAT 4224 from Elf Atochem and certain alcohol and amine functional tertiary amine catalysts such as methyldiethanolamine and tetramethylguanidine. In batch preparations from about 100 to about 1000 grams, one may use about 0.1 gram of FASTCAT 4224 per 100 gram of total resin.

The ratio of polyisocyanate to polyactive hydrogen compound is adjusted such that the prepolymer has a molecular weight of about 1000 to about 25000. The equivalents of polyisocyanate may exceed the total equivalents of polyactive hydrogen compound (i.e., total equivalents of active hydrogen), the equivalent excess being from about 1.1:1 to about 6:1, also from about 1.5:1 to about 3:1, and further also from about 1.8 to about 2.2.

Once the prepolymer is formed, the molecular weight should be increased to yield a composition with the desired properties. This step is accomplished by reacting the prepolymer with a "chain extender." As used herein the term "chain extender" means a polyactive hydrogen compound having a functionality of about 2 to about 4, also of about 2 to about 3, and further also about 2 and generally having a molecular weight of about 30 to about 2000, such as about 30 to about 1000. In one embodiment, the chain extenders are chosen from polyfunctional alcohols, amines, and carboxylic acid hydrazides. In another embodiment, the chain extenders are chosen from polyfunctional amines and carboxylic acid hydrazides.

Useful polyamines include ethylenediamine; 1,6-diaminohexane; piperazine; tris(2-aminoethyl)amine; and amine terminated polyethers such as those marketed as JEFFAMINE by the Huntsman Corporation, Salt Lake City, Utah, for example JEFFAMINE D230 and JEFFAMINE D400.

Useful carboxylic acid hydrazides include adipic acid dihydrazide and oxalic acid dihydrazides. Particularly useful polyfunctional alcohols include alkylene diols having 2 to 24 carbon atoms such as ethylene glycol; 1,4-butane diol; and 1,8-octane diol. Useful polythiols include 1,2-ethanedithiol; 1,4-butanedithiol; 2,2'-oxytris(ethane thiol) and di- and tri-mercaptopropionate esters of poly (oxyethylene) diols and triols. Water is also useful as a polyfunctional chain extender as it reacts with isocyanate to form an unstable carbamic acid, which loses carbon dioxide to liberate an amine. This amine is then available to react with another isocyanate.

When the prepolymer has a functionality of 2 or less and the chain extender is difunctional, the ratio of isocyanate to active hydrogen in the chain extension step is from about 0.6:1 to about 1.2:1, also from about 0.75:1 to about 1.0:1, and further also from about 0.80:1 to about 1.0:1 (except when water is used as the sole chain extender, in which case water can be present in large molar excess). When the prepolymer has a functionality higher than 2, due to the use of polyactive hydrogen compounds or polyisocyanates with a functionality greater than 2, it may perhaps be necessary to proportionately adjust downward the ratio of isocyanate to active hydrogen present in the chain extender to prevent gelation and keep the molecular weight of the polyurethane polymer formed in an appropriate region to provide reshapable hair styling performance.

In an environment with high concentrations of a lower alcohol (typically more than 20:80 w/w alcohol to water), endcapping of the isocyanate functional prepolymer may occur as the isocyanate reacts with the alcohol solvent. Therefore, use of a polyfunctional amine as the chain extender is highly suitable because amines are much more reactive toward isocyanate than the lower alcohol, giving better control of molecular weight.

In one embodiment, the dispersing medium may be chosen from lower alcohols ($C_1$ to $C_4$ branched or straight chain aliphatic alcohols), water, and mixtures thereof. The lower alcohols may be chosen from ethanol, n-propanol, and 2-propanol (IPA). Alternatively, the medium may be chosen from water, IPA, ethanol, and mixtures thereof. The alcohol to water ratio may range from 20:80 to 90:10 w/w and also from 70:30 to 85:15. In general, higher amounts of alcohol will result in a dispersion that exhibits faster dry times.

The solvent system may comprise other solvents. For example, other rapid evaporating, skin compatible solvents may be used, such as hexamethyldisiloxane (HMDS); cyclic silicones ($D_4$ and $D_5$); $C_4$–$C_{10}$ alkanes including isoparafins such as Permethyl 97A and Isopar C; acetone; hydrofluoroethers (HFEs) and the like. Certain HFEs, such as HFE 7100, have an added benefit in certain applications; when such as solvent is added to hydro-alcohol mixtures in levels above about 15 to about 25 wt %, the composition becomes non-flammable.

The reaction that forms the polyurethane polymer is stopped by the use of chain termination species (the chain terminator), used to stop the growing polymer chain thereby controlling the molecular weight and the physical properties of the polymer. In one embodiment, a diamine chain extender, used in excess, functions as a chain terminator. Another useful chain terminating agent is 2-amino-2-methyl-1-propanol (AMP), used in about 0.1 to about 2.0 parts, based on the total weight of the polyurethane polymer. Monofunctional amines or alcohols are useful as chain terminators. An example of a monofunctional alcohol is ethanol, which can further function as part of the dispersing medium.

The dispersions of the present invention may be prepared in any number of methods. In a first method, the prepolymer can be added to the solvent as 100% solids or diluted first with a different solvent that may or may not be removed later. If the solvent is to be removed, it may be more volatile than either water or the lower alcohol. In another method, the prepolymer can be dispersed in part of or in all of the solvent mixture or in a portion of the solvent mixture with subsequent addition of additional solvents. Any additional solvent added after dispersion could be added slowly in order to ensure the dispersion maintains stability. In yet another method, the prepolymer and/or dispersion solvent may be heated or cooled. In yet another method, the prepolymer may be dispersed in the solvent prior to, simultaneously with, or after the chain extender and chain terminator have been added to the solvent mixture.

One embodiment of the dispersion method involves heating the prepolymer to temperatures of about 45° C. to about 80° C. to reduce its viscosity. The heated prepolymer is added to a rapidly stirring high shear mixing apparatus, such as a homogenizer, containing the solvent. Thereafter, the amine, a chain extender, is added at a predetermined rate. Alternatively, for certain formulations, the amine can be added to the solvent mixture first and the heated prepolymer added to the rapidly mixing solvent mixture.

For an alcohol-water system, the level of lower alcohol may be at least 20% by weight, such as at least 40%, further such as at least 60%, and more further such as at least 70% by weight. In one embodiment, the level of lower alcohol is not more than 90%, such as not more than 85%.

The weight average molecular weight of the polyurethane in the final dispersion is generally about 5000 to about 50000, also about 15000 to about 35000, and further also about 20000 to about 30000.

In one embodiment, the method of controlling the level of reshapability may comprise adding monofunctional amines prior to or during the chain extension step. This method will result in end capping of some isocyanate groups thereby limiting the molecular weight. The monofunctional amines generally have the following structure:

$R_1R_2NH$ where $R_1$ and $R_2$, which are the same or different, are each chosen from a hydrogen atom and $C_1$ to $C_{22}$ alkyl, $C_6$ to $C_{28}$ aryl, and $C_6$ to $C_{28}$ aralkyl groups optionally substituted in available positions by N, O, and/or S groups, including alcohol, tertiary amine, quaternary amine, ketone, and carboxylic acid substitutions. In one embodiment, the monofunctional amines are those that would have low skin irritation if left unreacted in the formulation, such as 2-amino-2-methylpropanol or higher alkyl primary and secondary amines as well primary and secondary alkanolamines.

The formulations of the present invention may also include plasticizers that can be added either to the prepolymer directly or can be added to the solvent mixture. The use of plasticizers may allow for the use of less solvent, and therefore produce more rapidly drying films. Where plasticizers are used, the base prepolymer should be formulated to ensure the plasticized adhesive has sufficient tensile strength. This could require the use of lower molecular weight polyols (lower NCO equivalent weight prepolymers). Preferred plasticizers are cosmetically acceptable emollients such as those disclosed in U.S. Pat. No. 5,951,993 at column, 17 line 35 to column 21, line 6, whose disclosure is incorporated herein by reference.

An embodiment of the invention provides a reshapable hair styling composition comprising, in a cosmetic vehicle suitable for hair, at least one dispersion comprising at least one polyurethane, leading to a styling material following application to the fibers and drying.

It is a further subject of the invention to provide a method for treating hair, characterized in that the composition according to the invention is applied to the hair before during, or after the shaping of the hairstyle.

In another embodiment of the invention, the polyurethane has a glass transition temperature (Tg) ranging from about −100 to about 15° C. According to the present invention, the Tg of the polyurethane is obtained following the application of the polyurethane dispersion to a substrate and drying. The glass transition temperature is determined by the Differential Scanning Calorimetric method (DSC).

The composition according to the invention may comprise at least one other constituent, which is conventional in cosmetics, chosen from preservatives; perfumes; UV filters; active haircare agents; plasticizers; anionic, cationic, amphoteric, nonionic, and zwitterionic surfactants; hair conditioning agents such as silicone fluids, fatty esters, fatty alcohol, long chain hydrocarbons, emollients, lubricants, and penetrants such as lanolin compounds, protein hydrolysates, and other protein derivatives; anionic, cationic, amphoteric, nonionic, and zwitterionic polymers; dyes; tints; bleaches; reducing agents; pH adjusting agents; sunscreens; preservatives; thickening agents; and perfumes.

The appropriate cosmetically acceptable vehicle is adapted to the method of application selected. The vehicle preferably comprises an appropriate solvent to which may be added additives such as gelling agents, foaming agents, and silicones.

It is understood that the person skilled in the art will know how to choose the additional constituents and their amount in the composition according to the invention, such as the constituents of the vehicle, so as not to adversely affect or substantially affect its reshapable hair styling properties.

The compositions according to the invention can be provided in any form known from the prior art, which is appropriate for their application to the hair, including in the form of a vaporizable composition, mousse, gel, or lotion.

The composition may be in any of the conventional forms including, but not limited to, shampoos, hair rinses, permanent waving compositions, waving compositions, hair dye compositions, hair straightening compositions, hair fixing products, hair styling gel products, products to use before or after a hair dye treatment, products to use before or after a permanent waving treatment, hair straightening compositions, products to use before or after a hair straightening treatment, and fixing foams.

The composition according to the invention may be vaporizable, for example by a pump, or may be a pressurized aerosol composition. It may be vaporizable by a dispensing valve controlled by a dispensing head, which in turn comprises a nozzle, which vaporizes the aerosol composition. A vaporizable composition according to the invention comprises an appropriate solvent. Advantageously, the appropriate solvent comprises at least one solvent chosen from water and lower alcohols. In accordance with the invention, the term lower alcohol means a C1–C4 aliphatic alcohol, preferably ethanol.

When the vaporizable composition according to the invention is an aerosol composition, it additionally comprises an appropriate amount of propellant. The propellant comprises compressed or liquefied gases, which are normally employed for the preparation of aerosol compositions. Suitable gasses include compressed air, carbon dioxide, nitrogen, and gases, which are soluble or otherwise in the composition, such as dimethyl ether, fluorinated or non-fluorinated hydrocarbons, and mixtures thereof.

The present invention additionally provides an aerosol device comprising a vessel comprising an aerosol composition, which comprises on the one hand a liquid phase (or juice) comprising at least one hair styling material as described above in an appropriate medium and on the other hand a propellant, and a dispenser for dispensing said aerosol composition.

The present invention additionally provides a method of treating keratinous fibers, especially hair, in which the composition according to the invention as defined above is applied to the hair before, during, or after the shaping of the hairstyle.

The compositions according to the invention can be rinsed off or not rinsed off the hair.

The present invention additionally provides the use of a composition as defined above in, or for the preparation of, a cosmetic reshapable hair styling formulation.

The composition according to the invention can be provided in any form known from the prior art, which is appropriate for their application to the hair, including in the form of a vaporizable composition, a mousse, a gel, or a lotion.

The determination of whether a polyurethane dispersion can provide a reshapable hair styling composition can be determined by an in vivo test. Specifically, a composition is prepared comprising the polyurethane dispersion and a cosmetically acceptable medium. The medium may be chosen, for example, from water, lower alcohols such as ethanol, and mixtures thereof. The composition typically comprises from about 1% to about 12% by weight active material. The compositions may be in any form noted above, including lotions.

Where the composition is in the form of a lotion, for example, the in vivo test proceeds as follows. The hair of the model is washed and then divided into two symmetrical portions, the right and the left sides. The composition is applied to one side of the head of the model, while a reference composition is applied to the other side of the head. The reference composition may, for example, be chosen from water, an existing commercial product, or another composition under study. The hairdresser dries and styles both sides of the head. The two sides of the head are separately evaluated for the styling effect, the cometic properties, and the reshapable effect. For example, once dried, the hair is brushed in different directions to remove the original styling. The hair is then brushed to restore the original styling. The process of removing the styling, restoring the styling, and evaluating the success of restoring the styling is repeated at least one more time to determine whether the composition is a reshapable hair styling composition. A reshapable hair styling composition permits (1) the original hair styling to be restored after brushing and (2) the creation of a new hair styling after brushing, which may also be restored after brushing. If the composition to be evaluated is in another form, such as a shampoo or conditioner, the in vivo test can be appropriately modified by one skilled in the art.

It is understood that the person skilled in the art would recognize that not all formulations would provide reshapable effect for all hair types during in vivo testing and will know how to formulate and evaluate reshapable hair styling composition in view of the various hair parameters, such as length (short versus long), diameter (thin versus thick), structure (curly versus straight), condition (oily, dry, or normal); and whether the hair is colored, bleached, permed, or straightened. Thus, in vivo testing may require testing on 10–20 different individuals.

The invention may be understood more clearly with the aid of the non limiting examples which follow, and which constitute an advantageous embodiment of the compositions in accordance with the invention.

EXAMPLES

Hair compositions were produced with different polyurethanes.

1) Preparation of the Medium Soluble Polyactive Hydrogen Compounds

Preparation A

A mixture of dimethyl 5-sodiosulfoisophthalate (DMSSIP, 337.3 g, 1.14 mol, from E.I. DuPont de Nemours, Wilmington, Del.), diethylene glycol (DEG, 424 g, 3.99 mol, from Aldrich Chemical Co., Milwaukee, Wis.), and zinc acetate, (0.82 g, from Aldrich) was heated to about 180° C. and the methanol by-product was distilled from the reaction mixture. After 4.5 hours NMR analysis of the reaction product showed that less than about 1% residual methyl ester was present in the reaction product.

Dibutyltin dilaurate catalyst (1.51 g, 2.4 mmol, from Alfa Chemical Co., Ward Hill, Mass.) was added to the above reaction product, the temperature held at about 180° C., and epsilon-caprolactone (650 g, 5.7 mol, from Aldrich) was added portionwise over about a 30 minute period. When addition was complete, the reaction mixture was held at about 180° C. for 4 hours. The product is designated as preparation A.

Determination of the hydroxyl equivalent weight of the reaction product was done as follows. A 5.12 g sample of the product mixture was dissolved in 20 mL of methyl ethyl ketone (MEK). Isophorone disocyanate (3.13 g, 14.1 mmol, from Aldrich) and dibutyltin dilaurate (0.02 g) were added. The solution was heated for about 4 hours at about 80° C. The solution was cooled to room temperature. A solution of dibutyl amine (4 milliliter (mL) of a 1.72 molar solution in MEK) was added, and the solution stirred for 15 minutes. Then, 20 mL of methanol and 4 to 5 drops of Bromphenol Blue indicator were added, and the solution titrated to a yellow endpoint with 2.17 mL of a 1.0 molar hydrochloric acid solution in water. This corresponds to a hydroxyl equivalent weight of about 218 (theoretical hydroxyl equivalent weight for preparation A is 235).

Preparation B

A reactor equipped with a mechanical stirrer, nitrogen purge, and distillation apparatus was charged with dimethyl-5-sodiosulfoisophthalate (700 grams, 4.73 equivalents, from Du Pont, Wilmington, Del.), 400 molecular weight polyethylene glycol (1947 grams, 9.735 equivalents, from Union Carbide Corp.; Danbury, Conn.), and 425 molecular weight polypropylene glycol (1947 grams, 9.184 equivalents, from Arco Chemical Co.; Newton Square, Pa.). The reactor was heated to 345° F. (174° C.) and vacuum was applied on the reactor and held for about 1.5 hours. The vacuum was broken with nitrogen. Titanium butoxide (3.6 grams) was added and the mixture was heated to 430° F. (220° C.) and held for 3 hours while collecting methanol. The temperature was then reduced to 345° F. (174° C.) and vacuum was applied to the reaction mixture for one hour. The contents were subsequently cooled to 200° F. (93° C.) under nitrogen and drained to yield a clear, colorless liquid polyol. The measured OH equivalent weight of this polyol is 313 g/mole OH (theoretical OH of 305). The theoretical sulfonate equivalent weight of the polyol mixture is 1879 g polymer/mole sulfonate.

Preparation C

A 5-liter reaction vessel was charged with 4100 g polyethylene glycol-600 (13.67 equivalents) and 505.67 g dimethyl-5-sodiosulfoisophthalate (3.42 equivalents). The materials were dried under full vacuum at 100° C. for 1 hour. Tetrabutyl titanate (0.08 wt %) was subsequently added and the reaction was heated at 220° C. until approximately 85% of the theoretical methanol had been removed. The reaction temperature was reduced to 170° C. and held under vacuum for 1 hour resulting in a clear, light-yellow material. Calculated hydroxyl equivalent weight was 428, calculated sulfonate equivalent weight was 2632.

2) Preparation of the Polyurethane Dispersions

EXAMPLES 1 TO 3

Into a one-liter reactor was charged the following components to make a 600 gram batch: 120.6 g (1.09 NCO equivalents) isophorone diisocyanate; 147.6 g (0.089 OH equivalents) KRATON L-2203 hydrogenated polybutadiene diol (OH equivalent weight 1660) from Shell Chemical Co., Houston, Tex.; 296.4 g (0.291 OH equivalents) TERATHANE 2000 polytetramethylene oxide diol (OH equivalent weight 1020) from E.I. du Pont Co., Wilmington, Del.; 6 g (0.05 OH equivalents) SURFYNOL 104 surfactant, a diol, from Air Products, Lehigh Valley, Pa. (OH equivalent weight 113.2); and 24 g (0.110 equivalents) of preparation A prepared above. This hazy mixture was heated with stirring under nitrogen to about 80° C. and 0.5 g of dibutyl tin dilaurate catalyst was added. An exotherm to about 90.5° C. occurred, and the reaction was continued with stirring for about 2.5 hours at 80±5° C.

Then, 60 g aliquots (theoretically containing 58.5 milliequivalents of residual NCO) of the resulting product were added to 200 mL glass jars containing 1.48 g (49 milliequivalents of amine) ethylene diamine chain extender 76.5 g ethanol and 13.5 g water (85:15 ratio, Example 1), 67.5 g ethanol and 22.5 g water (75:25 ratio, Example 2), or 85.5 g ethanol and 4.5 g water (95:5 ratio, Example 3). Stirring at moderate speed yielded a milky white 40 wt % solids dispersion for all.

EXAMPLES 4 TO 8

Following the procedure used in Example 1, 78.8 g (47.5 milliequiv OH) KRATON L-2203 diol, 157.6 g (154.5 milliequiv OH) TERATHANE 2000 diol, 12.0 g (40 milliequiv OH) preparation B made above, and 51.5 g (464.3 milliequiv NCO) isophorone diisocyanate were charged into a 500 mL reactor and heated with stirring to about 80° C. under nitrogen. About two (2) drops of dioctyl tin dilaurate were added and an exotherm to about 87° C. was noted. After reacting for about 2½ hours, the mixture was cooled slightly and 30 g aliquots (with 22.2 milliequiv theoretical unreacted NCO) were charged into 100 mL jars containing 45 g of 85:15 ethanol to water solutions of ethylene diamine (EDA, chain extender) and 2-amino-2-methyl-1-propanol (AMP, chain terminator) in the following ratios (grams (mequiv)): 0.70 (23.3)/0 (0) for Example 4; 0.63 (21.0)/0.21 (2.3) for Example 5; 0.56 (1.87)/0.41 (4.6) for Example 6; 0.49 (1 6.3)/0.62 (7.0) for Example 7; 0.35 (11.7)/1.03 (11.6) for Example 8. These mixtures were homogenized with an Omni Macro Homogenizer from Omni International, Marietta, Ga., USA.

EXAMPLES 9 AND 10

Following the procedure used in Example 1, 46.7 g (28.1 milliequiv OH) KRATON L-2203 diol, 93.3 g (91.5 milliequiv OH) TERATHANE 2000 diol, 20.0 g (66.7 milliequiv OH) preparation B made above, and 40 g (360.4 milliequiv NCO) isophorone diisocyanate were charged into a 500 mL reactor and heated with stirring to about 80° C. under nitrogen. One drop of dioctyl tin dilaurate was added and an exotherm to about 82° C. was noted. After reacting for about 2 hours, the mixture was cooled slightly and 30 g aliquots (with 26.1 milliequiv theoretical unreacted NCO) were charged into 100 mL jars containing 45 g of 85:15 ethanol-water solution of 0.81 g EDA for Example 9 and 0.65 g (27 milliequiv) EDA and 0.48 g (5.4 milliequiv) AMP for Example 10. These mixtures were homogenized with an Omni Macro Homogenizer.

EXAMPLES 11 TO 13

Following the procedure used in Example 1, 36.8 g (22.2 milliequiv OH) KRATON L-2203 diol, 73.6 g (72.2 milliequiv OH) TERATHANE 2000 diol, 40.0 g (133.3 milliequiv OH) preparation B, and 49.6 g (446.8 milliequiv NCO) isophorone diisocyanate were charged into a 500 mL reactor and heated with stirring to about 80° C. under nitrogen. One (1) drop of dioctyl tin dilaurate was added and an exotherm to about 85° C. was noted. After reacting for about 2 hours, the mixture was cooled slightly and 30 g aliquots (with 32.9 milliequiv theoretical unreacted NCO) were charged into 100 mL jars containing 45 g of either water (Example 11), 85:15 ethanol-water solution of 1.00 g (33 milliequiv) EDA (Example 12), or 0.80 g (26.7 milliequiv) EDA and 0.60 g (6.7 milliequiv) AMP (Example 13). These mixtures were homogenized with an Omni Macro Homogenizer.

EXAMPLES 14 TO 17

Following the procedure used in Example 1 157.84 g (95.1 milliequiv OH) KRATON L-2203 diol, 315.45 g (309.3 milliequiv OH) TERATHANE 2000 diol, 24.39 g (81.3 milliequiv OH) preparation B, and 103.4 g (931.5 milliequiv NCO) isophorone diisocyanate were charged into a 500 mL reactor and heated with stirring to about 55° C. under nitrogen. Three (3) drops of dioctyl tin dilaurate were added and a slight exotherm was noted. The temperature was raised to about 80° C. and held there for about 2 hours. The mixture was cooled slightly and 90 g aliquots (with 67.2 milliequiv theoretical unreacted NCO) were charged into 500 mL jars containing 135 g of 85:15 ethanol-water solvent system containing ethylene diamine (EDA) and 2-amino-2-methyl-1-propanol (AMP) in various ratios: Example 14 (99 g (66.3 milliequivalents) EDA and 0 g AMP); Example 15 (1.88 g (62.7 miliequivalents) EDA and 0.31 g (3.5 miliequivalents) AMP); Example 16 (1.78 g (59.3 miliequivalents) EDA and 0.62 g (7.0 miliwequivalents) AMP); and Example 17 (1.57 g (52.3 miliequivalents) EDA and 1.24 g (13.9 miliequivalents) AMP). These mixtures were homogenized with an Omni Macro Homogenizer.

EXAMPLES 18 TO 20

Following the procedure used in Example 1, 78.85 g (47.5 milliequiv OH) KRATON L-2203 diol, 157.6 g (157.6 milliequiv OH) polypropylene glycol 2000 diol from EM Science, Gibbstown, N.J., USA, 12.2 g (40.7 milliequiv OH) preparation B, and 52.25 g (470.7 milliequiv NCO) isophorone diisocyanate were charged into a 500 mL reactor and heated with stirring to 80° C. under nitrogen. Two (2) drops of dioctyl tin dilaurate were added and an exotherm to 81° C. was noted. After reacting for 2 hours, the mixture was cooled slightly and 30 g aliquots (with 22.4 milliequiv theoretical unreacted NCO) were charged into 100 mL jars containing 45 g of 85:15 ethanol-water solvent mixtures containing EDA and AMP in the following ratios(grams (mequiv)): 0.66 (22.0)/0(0) for Example 18; 0.63 (21.0)/0.10 (1.1) for Example 19; 0.59 (1.97)/0.21 (2.4) for Example 20. These mixtures were homogenized with an Omni Macro Homogenizer.

EXAMPLES 21 TO 24

Following the procedure used in Example 1, 25 g (15.1 milliequiv OH) KRATON L-2203 diol, 50 g (40.5 milliequiv OH) TEXOX 5WL-1400 2470 molecular weight 75/25 ethylene glycol/propylene glycol random copolymer diol from Texaco Chemical, Houston, Tex., USA, 4 g (13.3 milliequiv OH) preparation B, and 15.3 g (137.8 milliequiv NCO) isophorone diisocyanate were charged into a 500 mL reactor and heated with stirring to about 80° C. under nitrogen. One (1) drop of dioctyl tin dilaurate was added and the reaction continued for about 2 hours. The mixture was cooled slightly and 20 g aliquots (with 14.7 milliequiv theoretical unreacted NCO) were charged into 100 mL jars containing 30 g of either water (Examples 21 and 22) or 85:15 ethanol-water solvent mixture (Examples 23 and 24) containing 0.42 g (14 milliequiv) EDA (Examples 21 and 23) or 0.37 g (12.3 milliequiv) EDA and 0.13 g (1.5 milliequiv) AMP (Examples 22 and 24). These mixtures were homogenized with an Omni Macro Homogenizer.

EXAMPLES 25 TO 27

Following the procedure used in Example 1, 26.4 g (15.9 milliequiv OH) KRATON L-2203 diol, 36.5 g (182.5 milliequiv OH) 400 molecular weight polyethylene glycol diol from Aldrich Chemical, 4.8 g (16.0 milliequiv OH) preparation B, and 31.1 g (280.2 milliequiv NCO) isophorone diisocyanate were charged into a 500 mL reactor and heated with stirring to about 80° C. under nitrogen. One (1) drop of dioctyl tin dilaurate was added and an exotherm to about 97° C. was noted. The reaction continued for about 1 hour during which time the viscosity increased.

The mixture was cooled slightly and 20 g aliquots (with 13.3 milliequiv theoretical unreacted NCO) of the thick paste were charged into 100 mL jars containing 30 g of either water (Example 25) or 85:15 ethanol-water solution (examples 26 and 27) of 1.86 g (62.0 milliequiv) EDA (Examples 25 and 26) or 1.66 g (55.3 milliequiv) EDA and 0.58 g (6.5 milliequiv) AMP (Example 27). These mixtures were homogenized with an Omni Macro Homogenizer.

EXAMPLES 28 TO 33

Following the procedure used in Example 1, 40.4 g (24.3 milliequiv OH) KRATON L-2203 diol, 80.7 g (65.3 milliequiv OH) TEXOX WL-1400 2470 molecular weight 75/25 ethylene glycol/propylene glycol random copolymer diol from Texaco 10 70 Chemical, 6 g (13.3 milliequiv OH) preparation C, and 23.1 g (208.1 milliequiv NCO) isophorone diisocyanate were charged into a 500 mL reactor and heated with stirring to about 80° C. under nitrogen. One (1) drop of dioctyl tin dilaurate was added and the reaction exothermed to about 82° C.

After reacting for about 2 hours, the mixture was cooled slightly and 20 g aliquots (with 14.0 milliequiv theoretical unreacted NCO) were charged into 100 mL jars containing 30 g of either water (Examples 28–31) or 85:15 ethanol-water solution (Examples 36 and 37) of 0.40 g (Examples 28, 29, 30, and 32) or 0.41 g (Example 33) (13.3 or 13.7 milliequiv, respectively) EDA or 13.9 g (13.9 milliequiv) JEFFAMINE ED2001 2000 molecular weight polyethylene oxide diamine from Huntsman Corporation, Salt Lake City, Utah, USA (Example 31). TWEEN 40 and STANDAPOL ES2 surfactants were added at 2 wt. % actives to Examples 29 and 30, respectively. These mixtures were homogenized with an Omni Macro Homogenizer.

EXAMPLES 34 TO 37

Following the procedure used in Example 1, 78.8 g (47.5 milliequiv OH) KRATON L-2203 diol, 157.5 g (154 milliequiv OH) TERATHANE 2000 diol (T-2000), 12.2 g (40.7 milliequiv OH) preparation B, and 51.6 g (464 milliequiv NCO) isophorone diisocyanate were charged into a 500 mL reactor and heated with stirring to about 60° C. under nitrogen. 3 drops of dibutyl tin dilaurate was added and an exotherm to about 77° C. was noted. The reaction temperature was increased to 80° C. and held there for about 2 hours.

The mixture was cooled slightly and 50 g aliquots (with 40.0 milliequiv theoretical unreacted NCO) of the prepolymer were charged with stirring into 200 mL jars containing 60 g of a 85/15 ethanol/water mixture. A mixture of 1.04 g (34.7 milliequiv) EDA and with 1.9 mequiv of various amine terminators in 15 g of 85:15 ethanol-water were charged in one portion after the prepolymer is well dispersed. Specific amine terminators used were 0.17 g 2-amino-2-methyl-1-propanol (Example 34), 0.36 g dodecyl amine (Example 35), 0.52 g octadecyl amine (Example 36), and 0.77 g didodecyl amine (Example 37).

EXAMPLES 38 TO 41

Following the procedure used in Examples 34 through 37, 77.0 g (76.9 milliequiv OH) PRIPLAST 3197, a 2000 molecular weight polyester diol of dimer diacid and dimer diol from Uniqema, 154.0 g (151 milliequiv OH) TERATHANE 2000 diol, 12.2 g (40.7 milliequiv OH) preparation B, and 56.8 g (511 milliequiv NCO) isophorone diisocyanate were reacted and dispersed in the identical fashion.

EXAMPLES 42 TO 45

Following the procedure used in Examples 34 through 37, 78.8 g (47.5 milliequiv OH) KRATON L2203 diol, 154.0 g (152 milliequiv OH) 2200 molecular weight polypropylene glycol (PPG 2200), 12.2 g (40.7 milliequiv OH) preparation B, and 51.6 g (464 milliequiv NCO) isophorone diisocyanate were reacted and dispersed in the identical fashion.

EXAMPLES 46 TO 51

The prepolymers prepared for Examples 34 through 37 and 42 through 45 (with Terathane 2000 or PPG 2200 respectively) were reacted with varying amounts of ethylene diamine and aminomethylpropanol (grams/grams): 0.98/ 0.36 for Example 46, 1.02, 0.3 for Example 47, 1.00/0.23 for Example 48, 0.97/0.36 for Example 49, 0.99/0.23 for Example 50, and 1.02/0.16 for Example 51.

EXAMPLES 52 TO 55

Following the procedure used in Example 1, 25.6 g (20.5 milliequiv OH) polybutadiene polyol with an OH equivalent weight of 1250 and an average functionality greater than 2 sold under the tradename POLY bd by Elf Atochem, Philadelphia, Pa., 51.4 g (51.4 milliequiv OH) TERATHANE 2000 diol, 4.2 g (13.4 milliequiv OH) sulfopolyester diol B, and 18.9 g (170 milliequiv NCO) isophorone diisocyanate were charged into a 250 mL reactor and heated with stirring to about 60° C. under nitrogen. Two (2) drops of dioctyl tin dilaurate was added and an exotherm to about 71° C. was noted. The reaction temperature was increased to 80° C. and held there for about 2 hours.

The mixture was cooled slightly and 20 g aliquots (with 16.9 milliequiv theoretical unreacted NCO) of the prepolymer were charged with stirring into 100 mL jars containing 30 g of a 85/15 ethanol/water mixture containing varying amounts of EDA and AMP (grams/grams): 0.35/0.45 for Example 52, 0.3/0.6 for Example 53, 0.25/0.75 for Example 54, and 0.2/0.9 for Example 55.

EXAMPLES 56 THROUGH 75

Following the procedure used in Example 1, KRATON L-2203 diol and TERATHANE 2000 diol were reacted at various ratios with isophorone diisocyanate (IPDI) and assorted stabilizers including VARIQUAT K1215 cationic diol from Witco, 600 molecular weight polyethylene glycol, dimethylol propanic acid (DMPA), preparation B, or with no additional added stabilizer. The prepolymers were dispersed into ethanol water containing EDA chain extender and AMP chain terminator as detailed below.

TABLE I

Formulations for Examples 56 through 75

| Ex. | Prepolymer | | | | Dispersion | | |
|---|---|---|---|---|---|---|---|
| | KRATON (grams) | TERATHANE (grams) | Stabilizer (grams) | IPDI (grams) | EDA | AMP | ethanol/water ratio |
| 56 | 39.0 | 76.6 | 9 g Variquat | 26.3 | 0.71 | 0 | 85/15 |
| 57 | 39.0 | 76.6 | 9 g Variquat | 26.3 | 0.64 | 0.21 | 85/15 |
| 58 | 39.0 | 76.6 | 9 g Variquat | 26.3 | 0.57 | 0.41 | 85/15 |
| 59 | 34.0 | 69.4 | 15 g PEG 600 | 20.7 | 0.84 | 0 | 85/15 |
| 60 | 34.0 | 69.4 | 15 g PEG 600 | 20.7 | 0.76 | 0.25 | 85/15 |
| 61 | 34.0 | 69.4 | 15 g PEG 600 | 20.7 | 0.67 | 0.5 | 85/15 |
| 62 | 38.3 | 76.5 | 3 g DMPA | 32.2 | 0.87 | 0.4 | 85/15 |
| 63 | 38.3 | 76.5 | 3 g DMPA | 32.2 | 0.78 | 0.66 | 85/15 |
| 64 | 38.3 | 76.5 | 3 g DMPA | 32.2 | 0.7 | 0.92 | 85/15 |
| 65 | 28.2 | 55.8 | 0 | 16.2 | 0.59 | 0.2 | 100/0 |
| 66 | 28.2 | 55.8 | 0 | 16.2 | 0.59 | 0.2 | 85/15 |
| 67 | 57.3 | 28.7 | 0 | 14 | 0.38 | 0 | 100/0 |
| 68 | 57.3 | 28.7 | 0 | 14 | 0.3 | 0.22 | 100/0 |
| 69 | 21.2 | 21.2 | 0 | 7.6 | 0.33 | 0.24 | 100/0 |
| 70 | 21.2 | 21.2 | 0 | 7.6 | 0.33 | 0.24 | 85/15 |
| 71 | 8.3 | 33.2 | 0 | 8.5 | 0.36 | 0.27 | 85/15 |
| 72 | 4.1 | 37.1 | 0 | 8.8 | 0.38 | 0.28 | 85/15 |
| 73 | 4.1 | 37.1 | 0 | 8.8 | 0.38 | 0.28 | 70/30 |
| 74 | 3.8 | 34.6 | 2 g Preparation B | 9.6 | 0.41 | 0.31 | 85/15 |
| 75 | 3.8 | 34.6 | 2 g Preparation B | 9.6 | 0.41 | 0.31 | 70/30 |

EXAMPLE 76

A 25/75 mixture of the dispersion from Example 2 and a dispersion comprising AQ 1350 by the Eastman Chemical Co. as disclosed in WO 98/38969 was made.

EXAMPLE 77

A 50/50 mixture of the dispersion from Example 1 and a dispersion from Example 2 was made.

3) Preparation of the Hair Styling Compositions

Four hair styling compositions in accordance with the invention were prepared using the components and amounts in weight percent listed hereafter. The testing was conducted on several models with one part of the head receiving the reference composition and the other side of the head receiving the tested formulation. The compositions were applied to wet hair after shampooing. The hair was then dried, brushed, and evaluated.

Reference:

| | |
|---|---|
| AQ 1350 | 4% active material |
| Ethanol | 20% |
| Water | qsp 100% |

Formulation A:

| | |
|---|---|
| Example 1 | 4% active material |
| Ethanol | qsp 100% |

Formulation A imparted good hairstyling and a reshapable effect better than the reference with good cosmetic properties, such as soft hair with a good touch.

Formulation B:

| | |
|---|---|
| Example 2 | 4% active material |
| Ethanol | qsp 100% |

Formulation B imparted good hairstyling and a reshapable effect better than the reference with good cosmetic properties, such as soft hair with a good touch.

Formulation C:

| | |
|---|---|
| Example 15 | 4% active material |
| Ethanol | qsp 100% |

Formulation C imparted good hairstyling that is equivalent to the reference but a reshapable effect better than the reference. Good cosmetic properties were achieved.

Formulation D

| | |
|---|---|
| Example 77 | 4% active material |
| Ethanol | qsp 100% |

Formulation D imparted good hairstyling that is equivalent to the reference but a good reshapable effect that is not as good as the reference. Adequate cosmetic properties were achieved.

What is claimed is:

1. A reshapable hair styling composition comprising, in a cosmetic vehicle appropriate for hair, at least one dispersion comprising at least one polyurethane in a water and/or solvent medium, said at least one polyurethane being obtained by reacting:
   (a) an isocyanate terminated polyurethane prepolymer being obtained by reacting: (i) at least one polyactive hydrogen compound insoluble in the medium of the dispersion, wherein said polyactive hydrogen compound is chosen from alkyl, aryl, and aralkyl structures optionally substituted in and/or on the structure by N, O, and/or S groups; (ii) at least one polyisocyanate, and (iii) at least one polyactive hydrogen compound soluble in the medium of the dispersion,
   (b) at least one polyfunctional chain extender; and
   (c) at least one chain terminator,
       wherein said at least one polyurethane is not neutralized after the at least one polyurethane has been obtained by reacting (a), (b), and (c), and
       wherein said composition provides a reshapable effect.

2. The composition according to claim 1, further comprising at least one additional polymer.

3. The composition according to claim 2, wherein said at least one additional polymer is chosen from anionic, cationic, amphoteric, nonionic, and zwitterionic polymers.

4. The composition according to claim 1, wherein said medium of the dispersion is at least one compound chosen from water and alcohols.

5. The composition according to claim 5, wherein said alcohols are chosen from lower alcohols.

6. The composition according to claim 1, wherein said at least one medium insoluble polyactive hydrogen compound is chosen from oligomeric polyols and oligomeric polyamines having on average from about 1.6 to about 4 hydroxyl or amino groups.

7. The composition according to claim 1, wherein said at least one medium insoluble polyactive hydrogen compound is chosen from polybutadiene polyols, polyisoprene polyols, hydrogenated polybutadiene polyols, hydrogenated polyisoprene polyols, polyester polyols from dimer diacids, polyester polyols from dimer diols, and dimer diols.

8. The composition according to claim 1, wherein said prepolymer is obtained by reacting: (i) at least one polyactive hydrogen compound insoluble in the medium of the dispersion, wherein said polyactive hydrogen compound is chosen from alkyl, aryl, and aralkyl structures optionally substituted in and/or on the structure by N, O, and/or S groups; (ii) at least one polyisocyanate, (iii) at least one polyactive hydrogen compound soluble in the medium of the dispersion, and (iv) at least one monomeric polyactive hydrogen compound soluble in the medium of the dispersion chosen from C36 dimer fatty alcohols, ethylene glycol, propylene glycol, butylene glycol, hexamethylene glycol, diethylene glycol, 1,1,1-trimethylolpropane, pentaerythritol, and aminoethanol.

9. The composition according to claim 1, wherein said at least one polyisocyanate is chosen from aliphatic polyisocyanates and cycloaliphatic polyisocyanates.

10. The composition according to claim 1, wherein said at least one polyisocyanate is chosen from dicyclohexylmethane 4,4'-diisocyanate, 3,5,5-trimethyl-1-isocyanato-3-isocyanatomethylcyclohexane, tetramethylene diisocyanate, 1,3-bis(isocyanatomethyl)cyclohexane, 1,3-bis(1-isocyanato-1-methylethyl)benzene, diphenylmethane 4,4'-diisocyanate, 4,4',4"-triisocyanatotriphenylmethane, polymethylene polyphenylene polyisocyanate, toluene diisocyanate, hexamethylene diisocyanate, dodecamethylene diisocyanate, and m- and p-xylene diisocyanate.

11. The composition according to claim 1, wherein said at least one medium soluble polyactive hydrogen compound is chosen from (i) compounds comprising at least one ionic group, (ii) compounds comprising at least one moiety capable of forming an ionic group, and (iii) compounds comprising at least one group chosen from polyester, polyether, and polycarbonate groups having a ratio of 5:1 or less carbon atoms to each oxygen atom.

12. The composition of claim 11, wherein said at least one medium soluble polyactive hydrogen compound is chosen from cationic compounds having the following structure:

$$R\text{—}N^+(R_2)[(OCH_2CH_2)_nOH]_2X^-$$

wherein R is chosen from $C_1$–$C_{18}$ alkyl, $C_6$–$C_{18}$ aryl, and $C_6$–$C_{18}$ aralkyl structure optionally substituted in and/or on the structure by N, O, and/or S groups; $R_2$ is chosen from a hydrogen atom and $C_1$–$C_{18}$ alkyl groups; n is an integer from about 1 to about 200; and $X^-$ is chosen from halides, sulfates, methosulfates, ethosulfates, acetates, carbonates, and phosphates.

13. The composition of claim 11, wherein said at least one medium soluble polyactive hydrogen compound is chosen from compounds having the following structure:

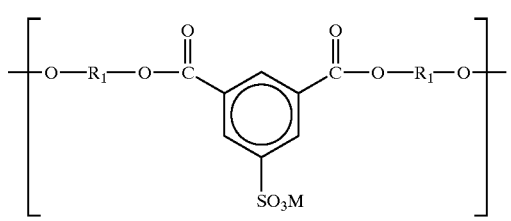

wherein M is a cation chosen from H, alkali metals, alkaline earth metals, and primary, secondary and tertiary ammonium cations; and each $R_1$ is the same or different and chosen from divalent aliphatic groups having an average molecular weight of about 200 to about 600 comprising ether and/or ester functional groups chosen from:

—$CH_2$—$CH_2$—($OCH_2$—$CH_2$—)$_n$—,

—$C(CH_3)H$—$CH_2$—($OC(CH_3)H$—$CH_2$—)$_n$—,

—$(CH_2)_4$—$(O(CH_2)_4)_n$—, and

—$(CH_2)_m$—CO—[—O—$(CH_2)_m$—CO—]$_n$— groups;

where m is an integer from about 2 to about 5 and n is an integer from about 2 to about 15.

14. The composition according to claim 1, wherein said prepolymer is obtained by reacting: (i) at least one polyactive hydrogen compound insoluble in the medium of the dispersion, wherein said polyactive hydrogen compound is chosen from alkyl, aryl, and aralkyl structures optionally substituted in and/or on the structure by N, O, and/or S groups; (ii) at least one polyisocyanate, (iii) at least one polyactive hydrogen compound soluble in the medium of the dispersion, and (iv) at least one monofunctional cationic stabilizer.

15. The composition according to claim 1, wherein said at least one polyfunctional chain extender is chosen from water; ethylenediamine, 1,6-diaminohexane, piperazine, tris (2-aminoethyl)amine, amine terminated polyethers, adipic acid dihydrazide, oxalic acid dihydrazide, ethylene glycol, 1,4-butane diol, 1,8-octane diol, 1,2-ethanedithiol, 1,4-butanedithiol, 2,2'-oxytris(ethane thiol), di-mercaptopropionate esters of poly(oxyethylene) diols, di-mercaptopropionate esters of poly(oxyethylene) triols, tri-mercaptopropionate esters of poly(oxyethylene) diols, and tri-mercaptopropionate esters of poly(oxyethylene) triols.

16. The composition according to claim 1, wherein said at least one chain terminator is chosen from monofunctional chain terminators.

17. The composition according to claim 1, wherein said at least one polyfunctional chain extender is also the at least one chain terminator.

18. The composition according to claim 17, wherein said at least one polyfunctional chain extender is chosen from diamine.

19. The composition according to claim 1, wherein the equivalent ratio of said chain extender to said prepolymer isocyanate is from about 0.60:1 to about 1.20:1.

20. The composition according to claim 1, wherein said at least one polyurethane dispersion has an ionic content of about 1000 to about 15000 gram of prepolymer per equivalent of an ionic group.

21. The composition according to claim 1, wherein said polyurethane reaction product has a weight average molecular weight of about 5000 to about 50000.

22. The composition according to claim 1, wherein the dispersion is a stable dispersion.

23. The composition according to claim 1, wherein the at least one polyurethane dispersion has a Tg ranging from about −100 to about 15° C.

24. The composition according to claim 1, further comprising at least one other constituent, which is conventional in cosmetics, chosen from preservatives, perfumes, UV filters, active haircare agents, plasticizers, anionic, cationic, amphoteric, nonionic, and zwitterionic surfactants, hair conditioning agents such as silicone fluids, fatty esters, fatty alcohol, long chain hydrocarbons, emollients, lubricants, and penetrants such as lanolin compounds, protein hydrolysates, and other protein derivatives, dyes, tints, bleaches, reducing agents, pH adjusting agents, sunscreens, preservatives, thickening agents, and perfumes.

25. An aerosol device comprising a vessel, which comprises (1) an aerosol composition, which comprises a liquid phase comprising at least one composition comprising at least one dispersion comprising at least one polyurethane in a water and/or solvent medium, said at least one polyurethane being obtained by reacting:

(a) an isocyanate terminated polyurethane prepolymer being obtained by reacting: (i) at least one polyactive hydrogen compound insoluble in the medium of the dispersion, wherein said polyactive hydrogen compound is chosen from alkyl, aryl, and aralkyl structures optionally substituted in and/or on the structure by N, O, and/or S groups; (ii) at least one polyisocyanate, and (iii) at least one polyactive hydrogen compound soluble in the medium of the dispersion, (b) at least one polyfunctional chain extender; and (c) at least one chain terminator,
wherein said at least one polyurethane is not neutralized after the at least one polyurethane has been obtained by reacting (a), (b), and (c), and
wherein said composition provides a reshapable effect, and a propellant, and (2) a dispenser.

26. A method of cosmetically treating hair, comprising the application of a composition comprising at least one dispersion comprising at least one polyurethane in a water and/or solvent medium, said at least one polyurethane being obtained by reacting:

(a) an isocyanate terminated polyurethane prepolymer being obtained by reacting: (i) at least one polyactive hydrogen compound insoluble in the medium of the dispersion, wherein said polyactive hydrogen compound is chosen from alkyl, aryl, and aralkyl structures optionally substituted in and/or on the structure by N, O, and/or S groups; (ii) at least one polyisocyanate, and (iii) at least one polyactive hydrogen compound soluble in the medium of the dispersion, (b) at least one polyfunctional chain extender; and (c) at least one chain terminator,
wherein said at least one polyurethane is not neutralized after the at least one polyurethane has been obtained by reacting (a), (b), and (c), and
wherein said composition provides a reshapable effect to the hair before, during, or after the shaping of the hairstyle.

27. A method of manufacturing a reshapable hair styling composition comprising the inclusion of at least one dispersion comprising at least one polyurethane in a water and/or solvent medium, said at least one polyurethane being obtained by reacting:

(a) an isocyanate terminated polyurethane prepolymer being obtained by reacting: (i) at least one polyactive hydrogen compound insoluble in the medium of the dispersion, wherein said polyactive hydrogen compound is chosen from alkyl, aryl, and aralkyl structures optionally substituted in and/or on the structure by N, O, and/or S groups; (ii) at least one polyisocyanate, and (iii) at least one polyactive hydrogen compound soluble in the medium of the dispersion, (b) at least one polyfunctional chain extender; and (c) at least one chain terminator,
wherein said at least one polyurethane is not neutralized after the at least one polyurethane has been obtained by reacting (a), (b), and (c), and
wherein said composition provides a reshapable effect.

* * * * *

UNITED STATES PATENT AND TRADEMARK OFFICE
CERTIFICATE OF CORRECTION

PATENT NO. : 6,613,314 B1
DATED : September 2, 2003
INVENTOR(S) : Isabelle Rollat et al.

It is certified that error appears in the above-identified patent and that said Letters Patent is hereby corrected as shown below:

<u>Title page,</u>
Item [75], Inventors, "Boulogne" should read -- Paris --.

<u>Column 19,</u>
Line 44, "claim 5," should read -- claim 4, --.

Signed and Sealed this

Thirteenth Day of January, 2004

JON W. DUDAS
*Acting Director of the United States Patent and Trademark Office*